United States Patent
Bossi et al.

(10) Patent No.: US 9,804,127 B2
(45) Date of Patent: Oct. 31, 2017

(54) LASER TESTING OF A BOND INTERFACE BETWEEN TWO DISSIMILAR MATERIALS

(71) Applicant: The Boeing Company, Chicago, IL (US)

(72) Inventors: Richard Henry Bossi, Renton, WA (US); Alan Frank Stewart, Seattle, WA (US); Marc Joel Piehl, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 332 days.

(21) Appl. No.: 14/515,818

(22) Filed: Oct. 16, 2014

(65) Prior Publication Data
US 2016/0109343 A1 Apr. 21, 2016

(51) Int. Cl.
| G01N 3/24 | (2006.01) |
| G01N 29/00 | (2006.01) |
| G01N 19/04 | (2006.01) |
| G01N 29/24 | (2006.01) |
| G01M 5/00 | (2006.01) |

(52) U.S. Cl.
CPC .......... *G01N 29/00* (2013.01); *G01M 5/0066* (2013.01); *G01N 19/04* (2013.01); *G01N 29/2418* (2013.01); *G01N 2291/02827* (2013.01); *G01N 2291/267* (2013.01)

(58) Field of Classification Search
CPC ................. G01N 29/11; G01N 29/14; G01N 2291/2694; G01N 2291/0231; G01N 29/045; G01N 19/04; G01N 29/2418; G01N 29/00; G01N 2291/02827; G01N 2291/267; G01N 3/317; G01N 29/2412; G01N 29/44; G01N 2291/0289; G01N 3/08; G01N 2203/0057; G01N 2203/005; G01N 3/00; G01N 2203/001; G01N 2203/0016

USPC ......... 73/588, 842, 766, 642, 760, 800, 827, 73/597, 844–845; 156/344; 29/402.03, 29/403.3; 702/43

See application file for complete search history.

(56) References Cited

U.S. PATENT DOCUMENTS

| 5,438,402 A | 8/1995 | Gupta |
| 6,848,321 B2 | 2/2005 | Bossi et al. |
| 8,359,924 B1 * | 1/2013 | Bossi ................... G01N 29/043 73/588 |
| 2005/0120803 A1 * | 6/2005 | Sokol ................. G01N 29/2412 73/801 |

(Continued)

OTHER PUBLICATIONS

Boustie et al., "Laser Shock Waves: Fundamentals and Applications," 1st International Symposium on Laser Science, Technology and Applications, Jul. 2008, 6 pages.

(Continued)

*Primary Examiner* — Harshad R Patel
*Assistant Examiner* — Brandi Hopkins
(74) *Attorney, Agent, or Firm* — Yee & Associates, P.C.

(57) ABSTRACT

A method and apparatus for testing a bond interface is provided. The method comprises directing laser energy at a first surface of a first material connected to a second material by an adhesive at a bond interface. The first surface is opposite the bond interface. A first acoustic impedance of the first material is greater than a second acoustic impedance of the second material. The method also determines whether an inconsistency is present in the bond interface after directing the laser energy.

13 Claims, 5 Drawing Sheets

(56) References Cited

U.S. PATENT DOCUMENTS

2005/0217388 A1* 10/2005 Heyman ............... G01N 3/32
73/827
2010/0005896 A1* 1/2010 Miller ............... B29C 65/8284
73/779

OTHER PUBLICATIONS

Yuan et al., "Measurement of interface strength by the modified laser spallation technique. I. Experiment and simulation of the spallation process," Journal of Applied Physics, vol. 74, Issue 4, Aug. 1993, pp. 2388-2396.

Gupta et al., "Experimental Techniques in the Dynamics: Nanosecond Rise-Time Stress Pulses Using Lasers for Applications to Material Characterization," American Society of Mechanical Engineers, AMD vol. 165, copyright 1993, pp. 61-70.

Bossi et al., "Using Shock Loads to Measure Bonded Joint Strength," Materials Evaluation, Nov. 2002, 14 pages.

Bossi et al., "Application of Stress Waves to Bond Inspection," SAMPE, May 2004, 14 pages.

Bossi et al., "Laser Bond Inspection," Materials Evaluation, vol. 67, No. 7, Jul. 2009, pp. 819-827.

Bossi, "Nondestructive Testing for Adhesive Bond Strength," Proceedings of the Adhesion Society, Feb. 2011, 3 pages.

Gupta et al., "Nanosecond Rise-Time Stress Pulses Using Lasers for Applications to Material Characterization," ASME, Experimental Techniques in the Dynamics of Deformable Solids, AMD—vol. 165, copyright 1993, pp. 61-70.

Bossi et al., "Bond Interface Testing," U.S. Appl. No. 12/828,519, filed Jul. 1, 2010, 32 pages.

Stewart et al., "Structural Bond Inspection," U.S. App. No. 14/080,753, filed Nov. 14, 2013, 42 pages.

* cited by examiner

LASER TESTING OF A BOND INTERFACE BETWEEN TWO DISSIMILAR MATERIALS

BACKGROUND INFORMATION

1. Field

The present disclosure relates generally to strength measurement of materials. More particularly, the invention relates to a non-destructive method and apparatus for measuring the strength of a bond interface between bonded structures.

2. Background

Bonded joints are widely used in a variety of structural applications, and more specifically, primary composite structures are often bonded together in select aerospace applications. The strength of the bonded joint between composite structures needs to be verified if the bonded joint is used in a primary structure application. Conventional measurement of bond strength generally involves static proof testing. For the structure to be used in aerospace service, structural proof testing can be performed to the limit load. Limit load is the maximum load that a structure is expected to see in service. However, the cost of such testing is usually high. Physical testing to failure to verify strength is more commonly performed using witness coupons. The witness coupons are samples that are assembled at the same time as the bonded joint using the same materials and following as closely as possible the bonding process of the real structure. The coupons are then tested to failure to verify process control and quality. While useful as an indicator, these test articles are not a part of the vehicle structure.

Non-destructive testing methods exist for composite structures; however, the non-destructive methods generally detect the presence of an inconsistency such as a void or disbond within a joint, not the strength thereof. Such methods may include, for example, ultrasonics, x-rays, and acoustics, among others commonly known in the art.

Laser bond inspection is a method of testing bonds using stress waves. The method involves depositing laser energy onto the front surface of a bonded article and generating compression stress waves that reflect off the back surface of the bonded article as tensile stress waves. The tensile waves predominantly provide the stresses that test the bond between similar materials. If a tensile wave of sufficient strength encounters a weak bond, the bond will separate. A tensile wave is a wave that causes tension in a material. Unfortunately, when the bond is between dissimilar materials, the wave reflected from the back surface may not create sufficient tension to evaluate the strength of the bond. Accordingly, physical testing to failure may be used to test the bond between dissimilar materials resulting in undesirable manufacturing time, undesirable manufacturing cost, or undesirable inconsistencies present in a part which are not detected.

Therefore, it would be desirable to have a method and apparatus that take into account at least some of the issues discussed above, as well as other possible issues. Specifically, one issue is to find a method and apparatus for testing a bond interface of dissimilar materials. Further, an issue is to find a method and apparatus for testing a bond interface of dissimilar materials from the surface of the material having the higher acoustic impedance.

SUMMARY

An illustrative embodiment of the present disclosure provides a method. The method comprises directing laser energy at a first surface of a first material connected to a second material by an adhesive at a bond interface. The first surface is opposite the bond interface. A first acoustic impedance of the first material is greater than a second acoustic impedance of the second material. The method also determines whether an inconsistency is present in the bond interface after directing the laser energy.

Another illustrative embodiment of the present disclosure provides another method. The method comprises transmitting an initial wave into a first surface of a first material connected to a second material by an adhesive at a bond interface. The first surface is opposite the bond interface. A first acoustic impedance of the first material is greater than a second acoustic impedance of the second material. The method also determines whether an inconsistency is present in the bond interface after transmitting the initial wave.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
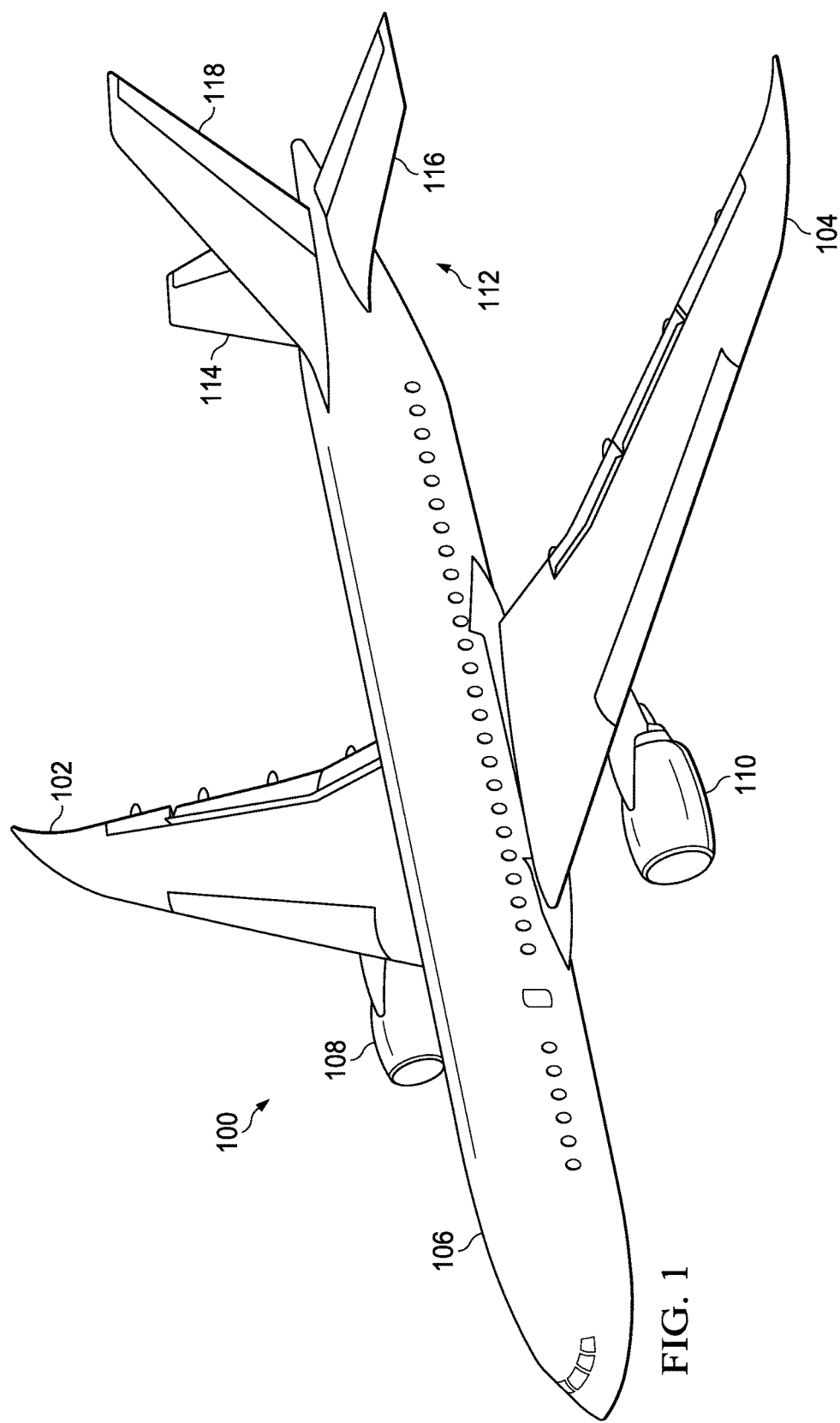
FIG. 1 is an illustration of an aircraft in which an illustrative embodiment may be implemented.

The illustrative embodiments recognize and take into account one or more different considerations. The different illustrative embodiments recognize and take into account that current non-destructive testing methods exist for composite structures. However, the illustrative embodiments also recognize and take into account that the current non-destructive methods generally detect the presence of a "visible" inconsistency, such as voids or foreign objects within a bond, not the strength of the bond itself. A "visible" inconsistency may be seen in at least one of a cross-section of the structure or images produced by a non-destructive method. Current non-destructive inspection methods may include, for example, ultrasonics, x-rays, and acoustics, among others commonly known in the art.

The different illustrative embodiments further recognize and take into account that laser bond inspection is a method of wave testing bonds which involves depositing laser energy onto the front surface of a bonded article and generating compression waves that reflect off the back surface of the bonded article as tensile waves. The tensile waves may predominantly provide the stresses that test the bond between similar materials. If a tensile wave of sufficient strength encounters a weak bond, the bond will be pulled apart.

The different illustrative embodiments also recognize and take into account that dissimilar materials may have different acoustic impedances. In this case, the above-mentioned process will not apply due to the impedance mismatch and reflections of the waves at the bond interface.

Further, the different illustrative embodiments also recognize that the current laser bond inspection may not have enough energy in the generated waves to test a bond interface when using dissimilar materials. When a compression wave is split at the bond interface, the transmitted wave and the reflected wave may travel to the exterior surfaces of the two materials and then back to the adhesive as tensile waves. The tensile waves separately may not provide enough energy to test the bond interface.

The different illustrative embodiments further recognize and take into account that in order to develop sufficient tension loads from waves in the bond between dissimilar materials in which the first material has a lower acoustic impedance, controlling the arrival time of the two waves may be done by modifying the thicknesses of the materials. Controlling the arrival time of the two waves may be used to peak a tension wave at the bond interface. In other words, tension may be created from a timing combination of a reflected wave in a first material and a transmitted wave in a second material.

The illustrative embodiments recognize and take into account that the inspection or bond testing of a structure having a composite material bonded to a metal is conventionally performed through the composite material. When directing a laser at the composite material, the laser energy may have a pulse width of about 100-300 nanosec. By having a pulse width of about 100-300 nanosec, the laser pulse may not spall composite material. When a composite material spalls, portions of the composite material may be broken or peeled off the remaining portions of the composite material. The illustrative embodiments recognize and take into account that the spalling of the composite material is undesirable. Accordingly, the illustrative embodiments recognize and take into account that lowering a pulse width of laser energy below 100 nanosec to test a structure including a composite material may be seen as undesirable.

The illustrative embodiments further recognize and take into account that sometimes the composite material side of a structure formed of the composite material bonded to a metal may not be accessible for inspection. The illustrative embodiments recognize and take into account that in these instances, it may be desirable to test the bond through the metal. However, the illustrative embodiments recognize and take into account that a substantial portion of an initial wave would be reflected at the bond interface. Thus, the illustrative embodiments recognize and take into account that the tensile waves reflected from the back surface of the composite material would be insufficient to test the strength of the bond interface.

Further, the illustrative embodiments recognize and take into account that the metal may act as a lossy resonator storing acoustic energy due to reflected waves within the metal. A lossy resonator may be similar to a bell continuing to ring after being struck. The illustrative embodiments recognize and take into account that the acoustic energy stored in the metal from using a laser pulse for testing a structure through a composite material may not be sufficient to test the bond. Specifically, the thickness of the metal may not allow sufficient pressure to build within the metal when using a laser pulse used for testing a structure through the composite material.

A method and apparatus for testing a bond interface is provided. The method comprises directing laser energy at a first surface of a first material connected to a second material by an adhesive at a bond interface. The first surface is opposite the bond interface. A first acoustic impedance of the first material is greater than a second acoustic impedance of the second material. The method also determines whether an inconsistency is present in the bond interface after directing the laser energy.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106.

Aircraft 100 is an example of an aircraft in which bond interface testing may be implemented in accordance with an illustrative embodiment. For example, a component of aircraft 100 may include a first material connected to a second material by an adhesive at a bond interface. In one illustrative example, wing 104 may include a metallic skin over a composite material. Bond testing or inspection of wing 104 may be inaccessible from the composite side.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, and other suitable types of aircraft.

Figure 2:
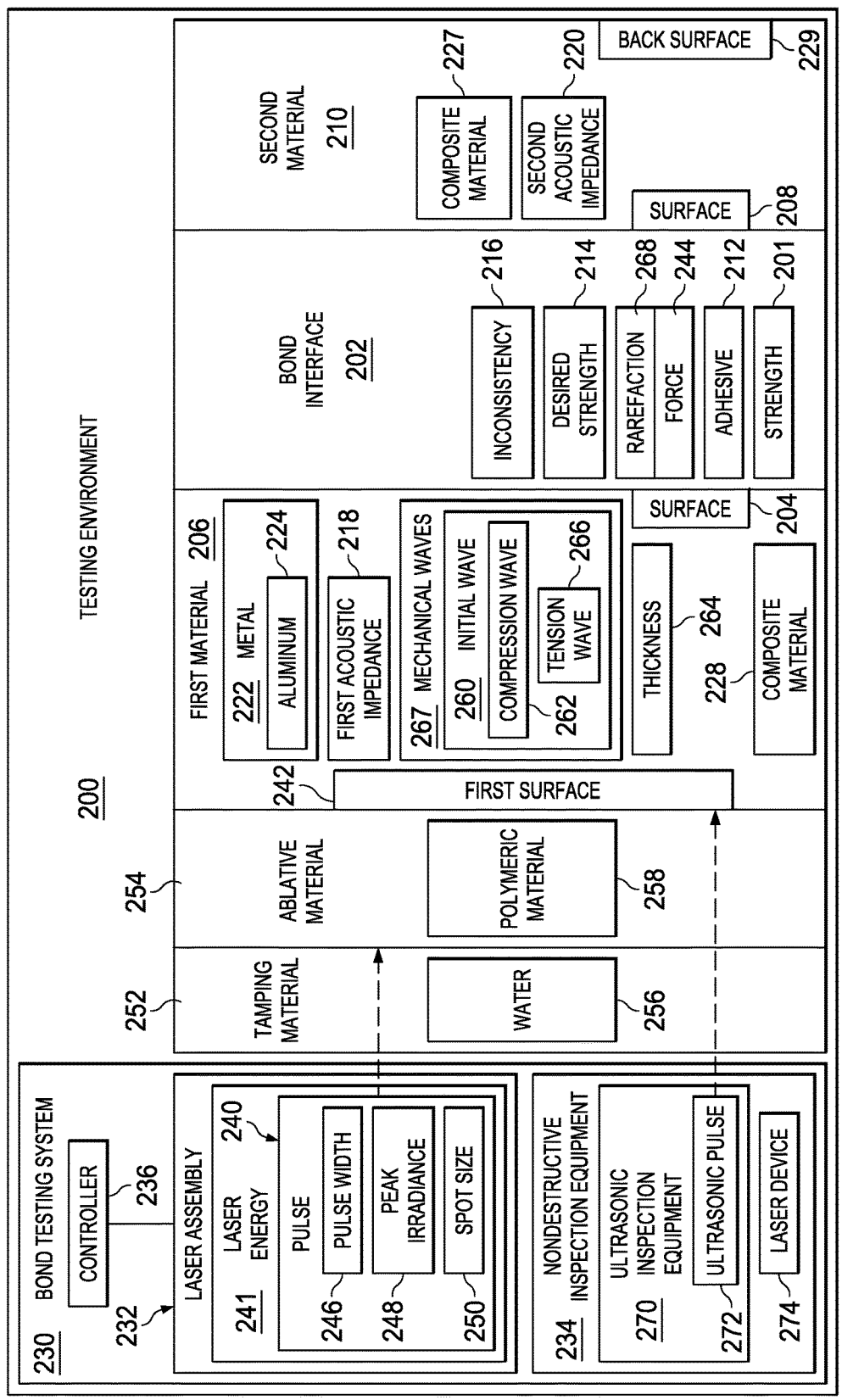
FIG. 2 is an illustration of a block diagram of a testing environment in accordance with an illustrative embodiment.

Turning now to FIG. 2, an illustration of a block diagram of a testing environment is depicted in accordance with an illustrative embodiment. Components of aircraft 100 of FIG. 1 may be tested in testing environment 200. Specifically, the bonds in the components of aircraft 100 of FIG. 1 may be tested in testing environment 200.

Testing environment 200 may be an environment in which the strength of a bond interface between two materials may be tested. For example, testing environment 200 may be an environment in which strength 201 of bond interface 202 may be tested. Bond interface 202 joins surface 204 of first material 206 and surface 208 of second material 210 using adhesive 212.

Adhesive 212 may be comprised of film or paste epoxy. An epoxy is a polymer formed from a reaction of a resin and a hardener. Adhesive 212 may be used to bond together two materials, such as, for example, first material 206 and second material 210. Adhesive 212 may have a thickness in the range of about 0.1 millimeters to about 0.62 millimeters. In some illustrative examples, adhesive 212 may have a thickness in the range of about 0.15 millimeters to about 0.2 millimeters. Adhesive 212 may be more elastic than first material 206. As a result, adhesive 212 may be more elastic and thus more lossy than first material 206. Adhesive 212 may be more prone to absorb acoustic energy than first material 206. As a result, it may be desirable for adhesive 212 to be relatively thin to reduce losses. For example, it may be desirable for adhesive 212 to be closer to about 0.1 millimeters in thickness than about 0.62 millimeters in thickness.

Bond interface 202 has desired strength 214. Desired strength 214 is a desired value for a strength of a bond between first material 206 and second material 210. Desired strength 214 may be based on performance characteristics for a structure formed of first material 206, second material 210, and adhesive 212. When inconsistency 216 is present in bond interface 202, strength 201 of bond interface 202 is less than desired strength 214.

First material 206 and second material 210 may be any type of material. In some illustrative examples, first material 206 and second material 210 are dissimilar materials. Dissimilar means the materials may have at least one of different densities or different acoustic impedances.

As used herein, the phrase "at least one of," when used with a list of items, means different combinations of one or more of the listed items may be used and only one of each item in the list may be needed. For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations. The item may be a particular object, thing, or a category. In other words, at least one of means any combination of items and number of items may be used from the list but not all of the items in the list are required.

First material 206 has first acoustic impedance 218. In some illustrative examples, first acoustic impedance 218 of first material 206 is greater than second acoustic impedance 220 of second material 210. In some illustrative examples, first material 206 may be a metal 222. In some illustrative examples, metal 222 may be aluminum 224. In other illustrative examples, metal 222 may be steel, titanium, or other desirable metals. Metal may have a thickness of about 0.4 millimeters to about 5 millimeters. In some illustrative examples, metal 222 may have a thickness of about 1 millimeter to about 3 millimeter.

In some illustrative examples, second material 210 may be composite material 227. Composite materials are tough, lightweight materials created by combining two or more functional components. For example, composite material 227 may include reinforcing fibers bound in polymer resin matrix. The fibers may be unidirectional or may take the form of a woven cloth or fabric. In some illustrative examples, first material 206 may be composite material 228 and second material 210 may be composite material 227.

Since first acoustic impedance 218 is greater than second acoustic impedance 220, a majority of the waves reaching bond interface 202 will reflect from bond interface 202. Thus, waves reflecting from back surface 229 of second material 210 may be insufficient to generate tension at bond interface 202. As a result, a different mechanism should be used to test strength 201 of bond interface 202.

Bond testing system 230 may be used to test strength 201 of bond interface 202. Bond testing system 230 includes laser assembly 232 and non-destructive inspection equipment 234. Laser assembly 232 may be any laser assembly configured to generate waves within first material 206. Laser assembly 232 may be directed by controller 236. Laser assembly 232 directs pulse 240 of laser energy 241 towards first surface 242 of first material 206.

Characteristics of pulse 240 are selected to generate force 244 on bond interface 202. Pulse 240 has pulse width 246, peak irradiance 248, and spot size 250. Pulse width 246 may be about 5 nanosec to about 15 nanosec. In some illustrative examples, pulse width 246 of laser energy 241 may be about 10 nanosec. Spot size 250 of laser energy 241 is about 2 mm to about 10 mm in diameter. Peak irradiance 248 of laser energy 241 may range from about 0.2 gigawatts/cm$^2$ to about 8 gigawatts/cm$^2$. Peak irradiance 248 is a measure used to describe the energy delivered to an area. Peak irradiance 248 is a measure of a beam energy of laser energy 241 divided by the product of multiplying the pulse duration by beam area. Peak irradiance 248 is also the peak power divided by beam area.

Laser energy 241 is directed at first surface 242 of first material 206. Laser energy 241 first encounters tamping material 252 and then ablative material 254. Ablative material 254 absorbs laser energy 241. By absorbing laser energy 241, ablative material 254 may generate a location of high mechanical energy. Tamping material 252 directs mechanical energy formed from laser energy 241 towards first surface 242. Tamping material 252 may confine the mechanical energy and direct it into first material 206, rather than allowing it to escape. Tamping material 252 may be selected to be transparent to laser energy 241. In some illustrative examples, tamping material 252 may take the form of water 256. In some illustrative examples, ablative material 254 may take the form of polymeric material 258. Polymeric material 258 may take the form of a poly vinyl chloride (PVC) tape, nylon, or other desirable material.

Mechanical energy generated in ablative material 254 is directed by tamping material 252 into first surface 242. The mechanical energy entering first surface 242 takes the form of initial wave 260. In this illustrative example, initial wave 260 is compression wave 262. Compression wave 262 may travel through thickness 264 of first material 206 to surface 204.

Unlike when first material 206 and second material 210 are similar materials, a substantial portion of initial wave 260 will reflect from surface 204 as tension wave 266. Tension wave 266 may be reflected from first surface 242. When tension wave 266 is reflected from first surface 242, it may be reflected as a compression wave that arrives back at surface 204. Further, like when first acoustic impedance 218 is lower than second acoustic impedance 220, very little of initial wave 260 will transmit through bond interface 202 to second material 210. The amount of initial wave 260 transmitted through bond interface 202 and reaching back surface 229 may be insufficient to form force 244 on bond interface 202 adequate to test or exercise the bond. Accordingly, to test strength 201 of bond interface 202, force 244 must be generated in a method different from when first material 206 and second material 210 are similar and also different from when first acoustic impedance 218 is less than second acoustic impedance 220.

Initial wave 260 may substantially reflect from surface 204. Initial wave 260 may substantially reflect from surface 204 as tension wave 266. Tension wave 266 is substantially internal to first material 206 and may not interact with adhesive 212 in bond interface 202. Tension wave 266 may be insufficient to generate force 244 for laser energy 241 having pulse width 246 of 100-300 nanosec. Further, tension wave 266 may be insufficient to cause displacement of surface 204.

Further, the reflected wave, tension wave 266, may substantially reflect again from first surface 242. Based on the reflecting of waves within first material 206, first material 206 may "ring" with waves. First material 206 "ringing" with waves may form a pressure within first material 206. However, thickness 264 may not be sufficient to generate force 244 on bond interface 202 with "ringing" within first material 206 generated by laser energy 241 having pulse width 246 of 100-300 nanosec.

Laser energy 241 may be tailored in order to test bond interface 202. For example, characteristics of laser energy 241, such as pulse width 246, peak irradiance 248, and spot size 250 may be selected based on at least one of thickness 264 of first material 206, type of material of first material 206, desired strength 214 of bond interface 202, or other desirable characteristic.

Compression wave 262 is generated when laser energy 241 is directed towards first surface 242 of first material 206. Compression wave 262 moves toward surface 204 of first material 206. Compression wave 262 may substantially reflect off bond interface 202 to form tension wave 266. When compression wave 262 substantially reflects from bond interface 202 as tension wave 266, this may cause rarefaction 268 at bond interface 202. Rarefaction 268 may also be based on a difference between first acoustic impedance 218 and second acoustic impedance 220. Rarefaction 268 may occur due to rapid changes in pressure on bond interface 202. Rarefaction 268 may "pull apart" bond interface 202.

Pulse width 246 may be selected to generate force 244 on bond interface 202. Specifically, pulse width 246 may be selected such that mechanical waves 267 generated within first material 206 have sufficient strength to cause rarefaction 268 at bond interface 202. Mechanical waves 267 may include at least one of compression wave 262 and tension wave 266.

Rarefaction 268 may occur at bond interface 202 as first material 206 pulls away rapidly from adhesive 212 that is still moving forward from compression wave 262. Rarefaction 268 occurs rapidly enough to create localized tension at bond interface 202 with enough force to open up or "pull apart" bond interface 202, causing inconsistency 216.

Compression wave 262 reflects from surface 204 of first material 206 as tension wave 266. At a high enough irradiance level, tension wave 266 can create an inconsistency or a disbond at surface 204 of first material 206. This inconsistency may take the form of a disbond. The inconsistency may be created because the particle velocity on surface 204 of first material 206 is high enough to create a disbond between first material 206 and adhesive 212 because of the difference between first acoustic impedance 218 and second acoustic impedance 220 which causes a difference in wave velocity in the two media.

Non-destructive inspection equipment 234 may be used to determine whether inconsistency 216 is present in bond interface 202 after directing laser energy 241. Non-destructive inspection equipment 234 may take the form of ultrasonic inspection equipment 270. Ultrasonic inspection equipment 270 may send ultrasonic pulse 272 into first surface 242 of first material 206. Ultrasonic pulse 272 will reflect from bond interface 202. When ultrasonic pulse 272 reaches inconsistency 216, ultrasonic pulse 272 will reflect differently than when ultrasonic pulse 272 reaches a portion of bond interface 202 not having an inconsistency. In some illustrative examples, ultrasonic inspection equipment 270 may send ultrasonic pulse 272 into back surface 229 of second material 210.

In some illustrative examples, non-destructive inspection equipment 234 may take the form of laser device 274. When rarefaction 268 causes inconsistency 216 in bond interface 202, vibrations that may be measured from the surfaces of either first material 206 or the second material 210 may be substantially different than if no inconsistency occurs. To measure vibrations, laser device 274 may be positioned to take readings of vibrations coming from first surface 242 of first material 206. Laser device 274 may be a type of laser configured to measure vibrations. In different embodiments, measurements may be taken by some other method or in a different location, such as on back surface 229 of second material 210.

In some illustrative examples, a non-destructive inspection may be performed after laser assembly 232 tests all of bond interface 202. In some other illustrative examples, a non-destructive inspection may be performed as laser assembly 232 tests bond interface 202. For example, a non-destructive inspection may be performed after each pulse 240 of laser energy 241 is directed towards first surface 242. In yet other illustrative examples, a portion of bond interface 202 may be tested by laser assembly 232 followed by the portion being non-destructively inspected.

Figure 3:
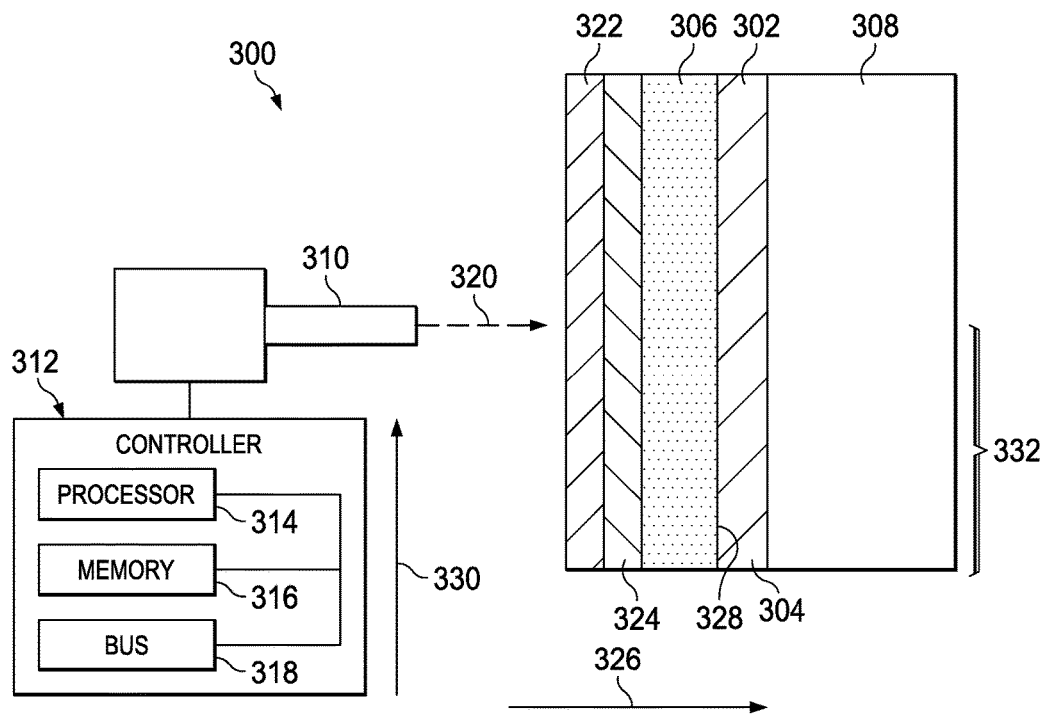
FIG. 3 is an illustration of a testing environment testing a structure without an inconsistency in a bond interface in accordance with an illustrative embodiment.

Turning now to FIG. 3, an illustration of a testing environment testing a structure without an inconsistency in a bond interface is depicted in accordance with an illustrative embodiment. Testing environment 300 may be a physical implementation of testing environment 200 of FIG. 2.

Testing environment 300 may be an environment in which the strength of a bond interface of materials may be tested. In this illustrative example, testing environment 300 is an environment in which the strength of bond interface 302 may be tested.

Bond interface 302 includes adhesive 304. Adhesive 304 bonds together first material 306 and second material 308. It is noted that the depicted size of adhesive 304 relative to first material 306 and second material 308 may not be indicative of the actual size used in practice. In some illustrative examples, adhesive 304 may have a thickness in the range of about 0.1 millimeters to about 0.62 millimeters. In some illustrative examples, adhesive 304 may be about 0.15 millimeters to about 0.2 millimeters. In some illustrative examples, adhesive 304 may be smaller than the ratios as depicted.

First material 306 and second material 308 may be any type of material. In one illustrative example, first material 306 and second material 308 may both be composite materials. In this illustrative example, the composite material of first material 306 has a higher acoustic impedance than the composite material of second material 308.

In other illustrative examples, first material 306 may be a metal while second material 308 may be a composite. In some illustrative examples, first material 306 may be aluminum.

Bond interface 302 is the location where first material 306 and second material 308 are joined together by adhesive 304. To test the strength of bond interface 302, laser 310 may transmit a wave into first material 306, adhesive 304, and second material 308. Laser 310 may be any laser configured to produce waves in adhesive 304, first material 306, and second material 308.

Controller 312 is used to control laser 310. Controller 312 may be any type of microcontroller or controller. Controller 312 comprises processor 314, memory 316, and bus 318. Processor 314 serves to execute instructions for software that may be loaded into memory 316. Processor 314 may be a number of processors, a processor unit, a multi-processor core, or some other type of processor, depending on the particular implementation. A number, as used herein with reference to an item, means one or more items. Further, processor 314 may be implemented using a number of heterogeneous processor systems in which a main processor is present with secondary processors on a single chip. As another illustrative example, processor 314 may be a symmetric multi-processor system containing multiple processors of the same type.

Memory 316 is an example of a storage device. A storage device is any piece of hardware that is capable of storing information, such as, for example, without limitation, data, program code in functional form, or other suitable information either on a temporary basis or a permanent basis. Memory 316 in these examples may be, for example, a random access memory or any other suitable volatile or non-volatile storage device.

Bus 318 may be a subsystem that transfers data between computer components. For example, bus 318 may be used to transfer data from processor 314 to memory 316.

As depicted, laser pulse 320 is directed towards first material 306. Laser pulse 320 enters tamping layer 322 and ablative material 324. Ablative material 324 absorbs laser pulse 320 and generates mechanical energy. The tamping layer 322 may substantially confine mechanical energy, forming a compression wave in first material 306. The compression wave travels in direction 326 towards bond interface 302. Upon reaching surface 328 of first material 306 at bond interface 302, the compression wave will be substantially reflected as a tension wave. As the compression wave is substantially reflected as the tension wave, rarefaction will be caused at bond interface 302 by the difference between the first acoustic impedance of first material 306 and the second acoustic impedance of second material 308. In this illustrative example, acoustic impedance of second material 308 is lower than the acoustic impedance of first material 306. This rarefaction will apply a force to bond interface 302. If bond interface 302 has a strength equal to or greater than the desired strength, an inconsistency will not be generated. If bond interface 302 has a strength less than the desired strength, an inconsistency will be generated.

As depicted, laser 310 may move in direction 330 testing bond interface 302 at various locations. In this illustrative example, tested region 332 has already been tested by laser 310. As depicted, tested region 332 does not have an inconsistency present. In other words, bond interface 302 within tested region 332 has a strength at least equal to the desired strength.

Figure 4:
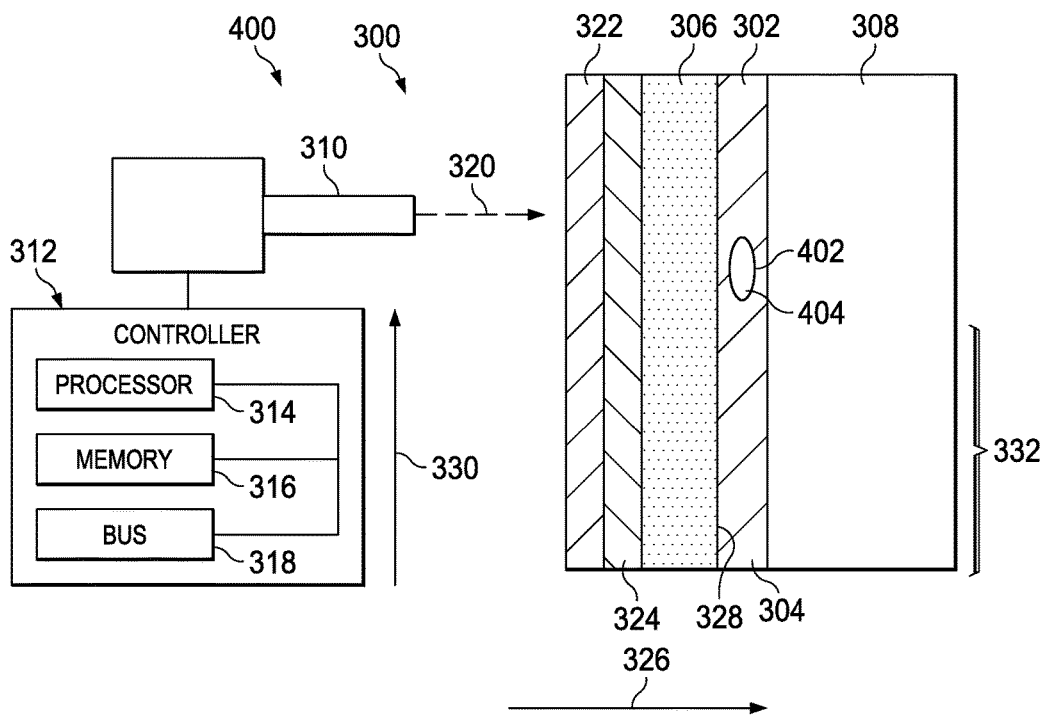
FIG. 4 is an illustration of a testing environment testing a structure with an inconsistency in a bond interface in accordance with an illustrative embodiment.

Turning now to FIG. 4, an illustration of a testing environment testing a structure with an inconsistency in a bond interface is depicted in accordance with an illustrative embodiment. View 400 is a view of testing environment 300 after laser 310 has moved in direction 330. In this illustrative example, testing bond interface 302 using laser 310 has generated inconsistency 402. In area 404 of inconsistency 402, bond interface 302 had a strength less than the desired strength. As a result, the rarefaction at bond interface 302 in area 404 pulled about bond interface 302 in area 404 causing inconsistency 402.

A non-destructive inspection technique may be used to determine whether an inconsistency, such as inconsistency 402, is present in bond interface 302. In some illustrative examples, the non-destructive inspection may be performed after all of first material 302 has been tested using laser 310. In other illustrative examples, the non-destructive inspection may be performed in each area of bond interface 302 following directing the energy of laser 310 at that area. In these illustrative examples, the non-destructive inspection may be performed prior to laser 310 moving in direction 330 to test another area of bond interface 302.

Figure 5:
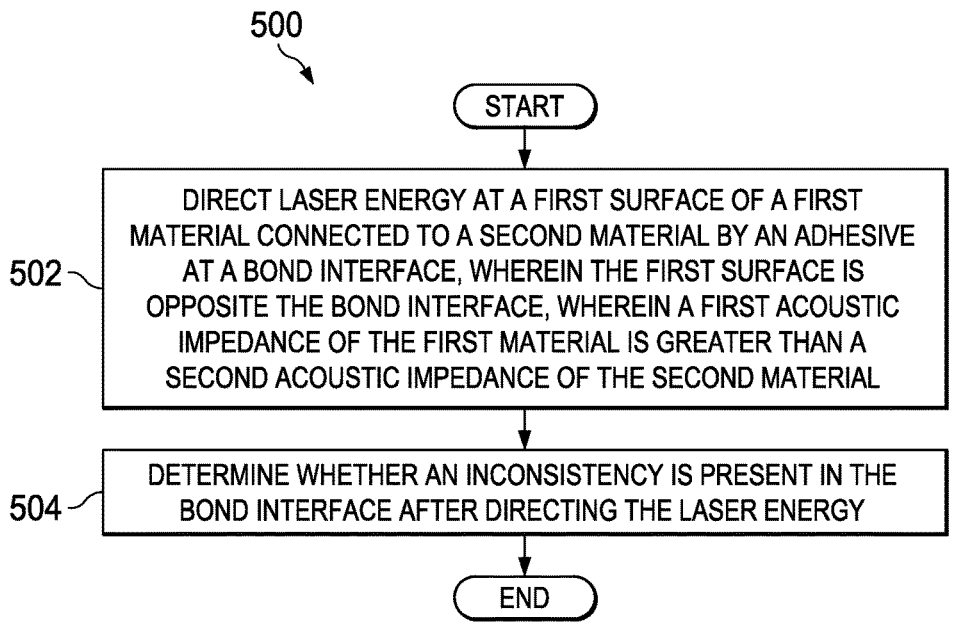
FIG. 5 is an illustration of a flowchart of a process for testing a structure in accordance with an illustrative embodiment.

Turning now to FIG. 5, an illustration of a flowchart of a process for testing a structure is depicted in accordance with an illustrative embodiment. Process 500 may be used to test a bond interface such as bond interface 202 of FIG. 2. Process 500 may be used to test a bond interface of a component or a structure, such as wing 104 of aircraft 100 of FIG. 1.

Process 500 begins by directing laser energy at a first surface of a first material connected to a second material by an adhesive at a bond interface, wherein the first surface is opposite the bond interface, wherein a first acoustic impedance of the first material is greater than a second acoustic impedance of the second material (operation 502). The laser energy may be tailored to produce a sufficient force to test the bond interface. Specifically, at least one of pulse width, peak irradiance, or spot size of the laser energy may be selected to generate a sufficient force to test the bond interface. In some illustrative examples, a pulse width of the laser energy is selected such that mechanical waves generated within the first material have sufficient strength to cause rarefaction at the bond interface. Mechanical waves may include a compression wave. In some illustrative examples, the spot size of the laser energy is about 2 mm to about 10 mm in diameter. In some illustrative examples, the peak irradiance of the laser energy ranges from about 0.2 gigawatts/cm$^2$ to about 8 gigawatts/cm$^2$. In some illustrative examples, a pulse width of the laser energy is between about 5 nanosec and about 15 nanosec. In one illustrative example, a pulse width of the laser energy is about 10 nanosec. Directing the laser energy may generate mechanical waves within the first material that cause rarefaction at the bond interface. The mechanical waves may comprise an initial wave. The initial wave may take the form of a compression wave. This rarefaction at the bond interface may cause inconsistencies in the bond interface if the strength of the bond interface is less than a desired strength.

In some illustrative examples, generating mechanical waves within the first material comprises directing the laser energy at an ablative material on the first surface of the first material such that an initial wave is transmitted into the first surface of the first material. In some illustrative examples, the initial wave is a compression wave, and generating mechanical waves within the first material further comprises reflecting the compression wave from the bond interface as a tension wave and causing rarefaction at the bond interface based on a difference between the first acoustic impedance and the second acoustic impedance.

Process 500 may then determine whether an inconsistency is present in the bond interface after directing the laser energy (operation 504). Afterwards, the process terminates. Determining whether an inconsistency is present in the bond interface may include performing a non-destructive inspection. Non-destructive inspections may be performed using one of ultrasonics, x-rays, and acoustics, or another desirable non-destructive method. In some illustrative examples, determining whether an inconsistency is present in the bond interface comprises sending ultrasonic pulse into the first material from the first surface.

Figure 6:
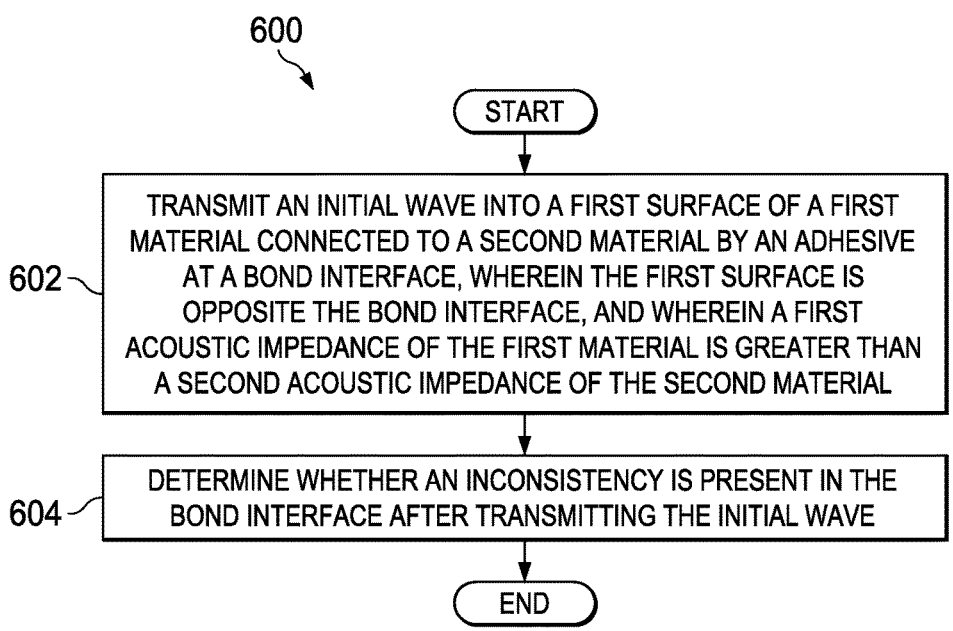
FIG. 6 is an illustration of a flowchart of a process for testing a structure in accordance with an illustrative embodiment.

Turning now to FIG. 6, an illustration of a flowchart of a process for testing a structure is depicted in accordance with an illustrative embodiment. Process 600 may be used to test a bond interface such as bond interface 202 of FIG. 2. Process 600 may be used to test a bond interface of a component or a structure, such as wing 104 of aircraft 100 of FIG. 1.

Process 600 begins by transmitting an initial wave into a first surface of a first material connected to a second material by an adhesive at a bond interface, wherein the first surface is opposite the bond interface, and wherein a first acoustic impedance of the first material is greater than a second acoustic impedance of the second material (operation 602). In some illustrative examples, the initial wave is a compression wave, and rarefaction from reflection of the compression wave at the bond interface causes an inconsistency if insufficient strength exists at the bond interface.

Process 600 may then determine whether an inconsistency is present in the bond interface after transmitting the initial wave (operation 604). Afterwards, the process terminates. Determining whether an inconsistency is present in the bond interface may include performing a non-destructive inspection. Non-destructive inspections may be performed using one of ultrasonics, x-rays, and acoustics, or another desirable non-destructive method. In some illustrative examples, determining whether an inconsistency is present in the bond interface comprises sending an ultrasonic pulse into the first material from a surface of the first material opposite the bond interface.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram. Further, some blocks may not be implemented.

For example, in some illustrative examples, process 600 may also direct laser energy at an ablative material on the first surface of the first material, wherein the first surface of the first material is opposite the bond interface. The ablative material may absorb the laser energy, thus creating mechanical energy.

The laser energy may be tailored to produce sufficient force to test the bond interface. Specifically, at least one of pulse width, peak irradiance, or spot size of the laser energy may be selected to generate a sufficient force to test the bond interface. In some illustrative examples, a pulse width of the laser energy is selected such that mechanical waves generated within the first material have sufficient strength to cause rarefaction at the bond interface. In some illustrative examples, the spot size of the laser energy is about 2 mm to about 10 mm in diameter. In some illustrative examples, the peak irradiance of the laser energy ranges from about 0.2 gigawatts/cm$^2$ to about 8 gigawatts/cm$^2$. In some illustrative examples, a pulse width of the laser energy is between 5 nanosec and about 15 nanosec. In one illustrative example, a pulse width of the laser energy is about 10 nanosec.

Figure 7:
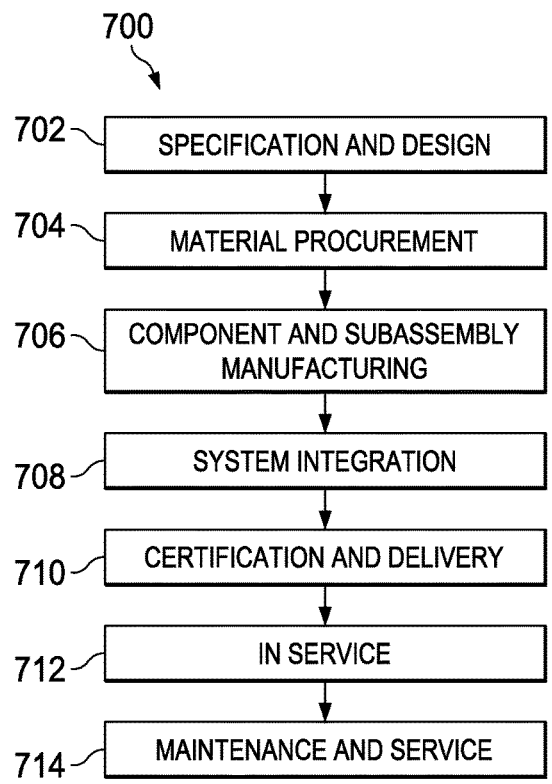
FIG. 7 is an illustration of a block diagram of an aircraft manufacturing and service method in accordance with an illustrative embodiment.
Figure 8:
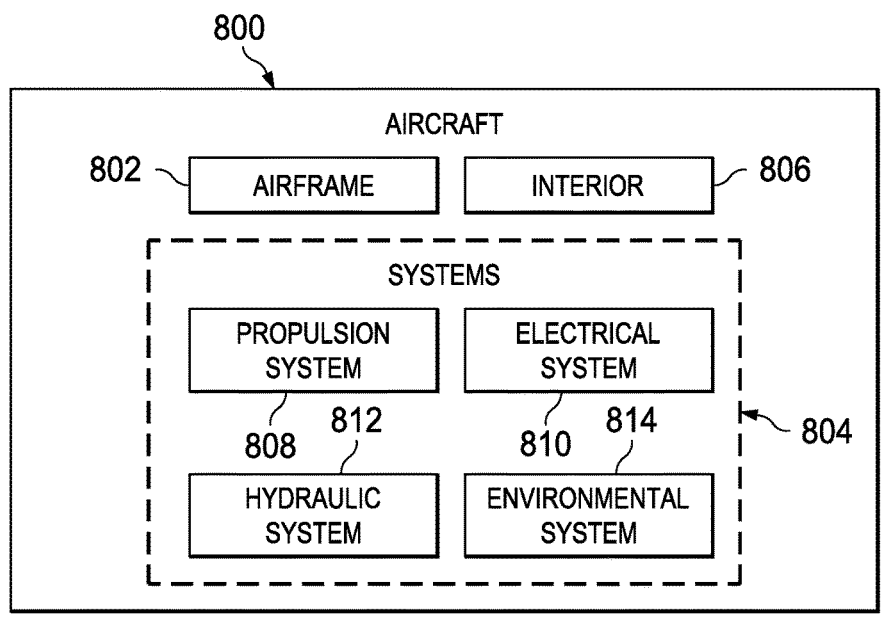
FIG. 8 is an illustration of a block diagram of an aircraft in which an illustrative embodiment may be implemented.

Illustrative embodiments of the disclosure may be described in the context of aircraft manufacturing and service method 700 as shown in FIG. 7 and aircraft 800 as shown in FIG. 8. Turning first to FIG. 7, an illustration of a block diagram of an aircraft manufacturing and service method is depicted in accordance with an illustrative embodiment. During pre-production, aircraft manufacturing and service method 700 may include specification and design 702 of aircraft 800 in FIG. 8 and material procurement 704.

During production, component and subassembly manufacturing 706 and system integration 708 of aircraft 800 in FIG. 8 takes place. Thereafter, aircraft 800 in FIG. 8 may go through certification and delivery 710 in order to be placed in service 712. While in service 712 by a customer, aircraft 800 in FIG. 8 is scheduled for routine maintenance and service 714, which may include modification, reconfiguration, refurbishment, and other maintenance or service.

Each of the processes of aircraft manufacturing and service method 700 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 8, an illustration of a block diagram of an aircraft is depicted in which an illustrative embodiment may be implemented. In this example, aircraft 800 is produced by aircraft manufacturing and service method 700 in FIG. 7 and may include airframe 802 with plurality of systems 804 and interior 806. Examples of systems 804 include one or more of propulsion system 808, electrical system 810, hydraulic system 812, and environmental system 814. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 700 in FIG. 7. One or more illustrative embodiments may be used during component and subassembly manufacturing 706. For example, aircraft manufacturing and service method 700 of FIG. 7 may be implemented using bond testing system 230 of FIG. 2 during component and subassembly manufacturing 706. Further, bond testing system 230 may also be used to test replacements prior to or during maintenance and service 714.

Although the different illustrative embodiments have been described with respect to parts for aircraft, other illustrative embodiments may be applied to parts for other types of adhesive and bonding strength test environments. For example, without limitation, other illustrative embodiments may be applied to bonds for spacecraft or any type of object where two materials are bonded together by an adhesive.

The different illustrative embodiments provide for bond interface strength testing for bonds between different materials. The testing provides for waves input into the first material to create a tension significant enough at the bond interface to pull apart a bond having a strength that is lower than a desired strength.

Thus, the illustrative embodiments provide a method and apparatus for testing a bond strength. Specifically, the illustrative embodiments provide a method and apparatus for testing a strength of a bond interface joining a first material and a second material, in which the first material has a greater acoustic impedance than the second material.

The illustrative examples set a pulse width of a laser assembly such that a force is created at the bond interface that can test the bond interface. In the illustrative examples, a pulse width of the laser energy may be about 10 nanosec. This pulse may be significantly narrowed from the wider pulse of about 100 nanosec to about 300 nanosec used in similar materials and bond interfaces in which the first material has lower acoustic impedance. In similar materials, the compression wave travels through the bond interface and second material to the back surface and reflects in tension. Normally a wide pulse of about 100 nanosec to about 300 nanosec is used to avoid back surface damage and create a tension wave in the structure.

For metal to composite bonds, a compression wave coming from the metallic side and generated using a wide pulse of about 100 nanosec to about 300 nanosec may not generate a force of sufficient strength to test the bond because of the reflection at the bond line and ringing of the compression wave in the metal layer. However, if the pulse width is narrowed, such as to between about 5 nanosec and about 15 nanosec, the peak irradiance applied can be higher. Further, if the pulse width is narrowed, the process of reflection of the tension wave at the adhesive interface will build very quickly and the surface of the first material will rebound quickly, creating a rarefaction and pulling away from the adhesive and the second material.

The illustrative embodiments present a method and an apparatus so that actual parts may be tested rather than witness coupons. Specifically, the illustrative embodiments present a method and apparatus so that actual parts may be tested from the side with the higher acoustic impedance. The illustrative embodiments may reduce one of manufacturing time, manufacturing cost, or parts with inconsistencies presented to customers.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for laser testing of a bond interface between two dissimilar materials, the method comprising:
   directing a pulse width of laser energy between about 5 nanosec to about 15 nanosec at a first surface of a first material connected to a second material by an adhesive at a bond interface, wherein the first surface is opposite the bond interface, wherein the first material and the second material are dissimilar and a first acoustic impedance of the first material is greater than a second acoustic impedance of the second material;
   wherein a compression wave is transmitted into the first surface of the first material and the compression wave is reflected from the bond interface as a tension wave to cause a rarefaction at the bond interface based on a difference between the first acoustic impedance and the second acoustic impedance; and
   wherein reflection of the tension wave at the bond interface builds very quickly and the first surface of the first material rebounds quickly creating the rarefaction and a pulling away from the adhesive and the second material.

2. The method of claim 1, further comprising:
   creating a tension load in the bond between the first material and the second material by a timing combination of a reflected wave in the first material and a transmitted wave in the second material, wherein a pulse width of the laser energy is selected such that mechanical waves generated within the first material have sufficient strength to cause rarefaction at the bond interface.

3. The method of claim 1, wherein the first material is a metal and the second material is a composite material.

4. The method of claim 3, wherein the metal has a thickness in a range of about 0.4 millimeters to about 5.0 millimeters.

5. The method of claim 1, wherein determining whether an inconsistency is present in the bond interface comprises sending ultrasonic pulse into the first material from the first surface.

6. The method of claim 1, wherein a spot size of the laser energy is about 2 millimeters to about 10 millimeters in diameter.

7. The method of claim 1, wherein a peak irradiance of the laser energy ranges from about 0.2 gigawatts/cm$^2$ to about 8 gigawatts/cm2.

8. A method comprising:
   transmitting an initial wave into a first surface of a first material connected to a second material by an adhesive at a bond interface, wherein the first surface is opposite the bond interface, and wherein a first acoustic impedance of the first material is greater than a second acoustic impedance of the second material;
   creating a tension load in the bond between the first material and the second material by a timing combination of a reflected wave in the first material and a transmitted wave in the second material; and
   determining whether an inconsistency is present in the bond interface after transmitting the initial wave;
   wherein the initial wave comprises laser energy having a pulse width between about 5 nanosec to about 15 nanosec;
   wherein a compression wave is transmitted into the first surface of the first material and the compression wave is reflected from the bond interface as a tension wave to cause a rarefaction at the bond interface based on a difference between the first acoustic impedance and the second acoustic impedance; and
   wherein reflection of the tension wave at the bond interface builds very quickly and the first surface of the first material rebounds quickly creating the rarefaction and a pulling away from the adhesive and the second material.

9. The method of claim 8, wherein the first material is a metal and the second material is a composite material.

10. The method of claim 9, wherein the metal has a thickness in a range of about 0.4 millimeters to about 5.0 millimeters.

11. The method of claim 8, wherein determining whether the inconsistency is present in the bond interface comprises sending an ultrasonic pulse into the first material from the first surface.

12. The method of claim 8, wherein a spot size of the laser energy is about 2 millimeters to about 10 millimeters in diameter.

13. The method of claim 8, wherein a peak irradiance of the laser energy ranges from about 0.2 gigawatts/cm2 to about 8 gigawatts/cm2.

\* \* \* \* \*